(12) United States Patent
Dalla-Torre et al.

(10) Patent No.: US 9,098,893 B2
(45) Date of Patent: Aug. 4, 2015

(54) SYSTEM, METHOD AND COMPUTER PROGRAM PRODUCT FOR CLASSIFICATION WITHIN INSPECTION IMAGES

(75) Inventors: Michele Dalla-Torre, Givataim (IL); Gil Shabat, Raanana (IL); Adi Dafni, Kibbutz Givat Brener (IL); Amit Batikoff, Petach Tikva (IL)

(73) Assignee: Applied Materials Israel, Ltd., Rehovot (IL)

( * ) Notice: Subject to any disclaimer, the term of this patent is extended or adjusted under 35 U.S.C. 154(b) by 120 days.

(21) Appl. No.: 13/333,912

(22) Filed: Dec. 21, 2011

(65) Prior Publication Data

US 2013/0163851 A1 Jun. 27, 2013

(51) Int. Cl.
*G06K 9/62* (2006.01)
*G06T 7/00* (2006.01)

(52) U.S. Cl.
CPC ....... *G06T 7/001* (2013.01); *G06T 2207/10061* (2013.01); *G06T 2207/30148* (2013.01)

(58) Field of Classification Search
None
See application file for complete search history.

(56) References Cited

U.S. PATENT DOCUMENTS

| 5,548,326 | A | * | 8/1996 | Michael | 348/87 |
| 5,699,447 | A | * | 12/1997 | Alumot et al. | 382/145 |
| 8,041,104 | B2 | * | 10/2011 | Toyoda et al. | 382/145 |
| 2007/0133860 | A1 | * | 6/2007 | Lin et al. | 382/149 |
| 2008/0317194 | A1 | * | 12/2008 | Gagnon et al. | 378/4 |
| 2010/0119144 | A1 | * | 5/2010 | Kulkarni et al. | 382/149 |
| 2011/0013825 | A1 | * | 1/2011 | Shibuya et al. | 382/149 |
| 2013/0016895 | A1 | * | 1/2013 | Song et al. | 382/149 |

\* cited by examiner

*Primary Examiner* — Aaron W Carter
*Assistant Examiner* — David F Dunphy
(74) *Attorney, Agent, or Firm* — Lowenstein Sandler LLP

(57) ABSTRACT

In accordance with an aspect of the presently disclosed subject matter, there is provided an analysis system for classifying possible defects identified within an inspection image of an inspected object, the system comprising a pattern matcher configured to determine an anchor location with respect to the inspection image, based on a matching of a template and a portion of the inspection image; wherein an accuracy of the determining of the anchor location exceeds a resolution of the inspection image; a distribution analysis module configured to determine, based on the anchor location and a mask which defines different segments within an area, a distribution of a potential defect with respect to one or more of the segments; and a classifier, configured to classify the potential defect based on the distribution.

14 Claims, 9 Drawing Sheets

10a
*Edge roughness*

10b
*Short Gate defect*

10c
*Edge roughness*

10d
*Short Gate defect*

SYSTEM, METHOD AND COMPUTER PROGRAM PRODUCT FOR CLASSIFICATION WITHIN INSPECTION IMAGES

FIELD OF THE INVENTION

This invention relates to systems and methods for classification within inspection images. Specifically, the invention may be implemented in the field of manufacturing of artifacts having minute details, such as wafers, photomasks, and electronic circuits.

BACKGROUND OF THE INVENTION

In many implementations, inspected objects are imaged and are searched thereafter to discover target patterns. For example, aerial images may be searched for enemy tanks, textile fabric imaged during manufacture may be searched for holes, and electronic circuits, such as wafers, may be imaged and searched for defects.

Taking the case of defects searched during manufacture of wafers as an example, it is clear that while defects can damage the proper operability of the electronic circuit, impact of different defects on the operation of the electronic circuit may vary. Therefore, some defects may be of no substantial interest to the inspecting party, e.g. if their impact on circuit operation is low. Furthermore, knowledge regarding the different defects may be useful for manufacturing of future similar electronic circuits.

FIGS. 1A and 1B illustrate two types of defects in an electronic circuit, wherein each of FIGS. 1A and 1B illustrates an electronic circuit (such as a wafer), scanned using electron beam inspection. The grey level in each one of the circuits illustrated in FIGS. 1A and 1B is indicative of the pattern of the electronic circuit in that part of the wafer. For example, materials of different conductivity (such as a conducting material and an isolating material) may have different reflection indexes which may be translated to different grey levels. The following discussion pertains to an example in which substantially different grey level values in the image are indicative of different materials of substantially different electrical conductivity.

Defects 10a and 10c (also denoted "edge roughness" defects) are located on the boundary of an area of the imaged layer of the wafer between two different materials. Therefore, the electronic effect of such a defect is relatively limited, and under some circumstances such a defect may be of little interest.

Defects 10b and 10d, on the other hand (also denoted "short gate" defects), are located between two areas of the imaged layer of similar materials, and may indicate a conductive connection between two parts of the electronic circuits which ought to be isolated from each other. Since the electronic effects of such a defect may be relatively significant, under some circumstances such a defect may be further inspected—e.g. in a higher inspection resolution and/or using slower and more in-depth image analysis.

SUMMARY OF THE INVENTION

In accordance with an aspect of the presently disclosed subject matter, there is provided an analysis system for classifying possible defects identified within an inspection image of an inspected object, the system comprising a pattern matcher configured to determine an anchor location with respect to the inspection image, based on a matching of a template and a portion of the inspection image; wherein an accuracy of the determining of the anchor location exceeds a resolution of the inspection image; a distribution analysis module configured to determine, based on the anchor location and a mask which defines different segments within an area, a distribution of a potential defect with respect to one or more of the segments; and a classifier, configured to classify the potential defect based on the distribution.

In accordance with an embodiment of the presently disclosed subject matter, there is further provided a system, wherein the inspected object is selected from a group consisting of an electronic circuit, a wafer, and a photomask.

In accordance with an embodiment of the presently disclosed subject matter, there is further provided a system, wherein the distribution analysis module is configured to determine the distribution at an accuracy which exceeds the resolution of the inspection image.

In accordance with an embodiment of the presently disclosed subject matter, there is further provided a system, wherein the different segments correspond to parts of the inspected object having different physical characteristics.

In accordance with an embodiment of the presently disclosed subject matter, there is yet further provided a system, wherein the classifier is configured to classify the potential defect according to a classification in which classes correspond to defect types whose implications on an operability of the inspected object differ.

In accordance with an embodiment of the presently disclosed subject matter, there is yet further provided a system, wherein the pattern matcher is configured to determine multiple anchor locations with respect to the inspection image, based on matching of the template and multiple portions of the inspection image; wherein accuracies of the determining of the multiple anchor locations exceed the resolution of the inspection image; wherein the distribution analysis module is configured to determine distributions of the potential defect with respect to at least one segment of the mask based on the mask and on the multiple anchor locations; wherein the classifier is configured to classify the potential defect based on multiple distributions determined for the potential defect by the distribution analysis module.

In accordance with an embodiment of the presently disclosed subject matter, there is yet further provided a system, wherein the classifier is further configured to select for further scanning potential defects which are classified into certain classes, wherein the selecting includes refraining from selecting potential defects classified into at least one class other than the certain classes; wherein the system further comprises an inspection module, configured to selectively scan, in a resolution which is higher than the resolution of the inspection image, at least one area of the inspected object which is selected based on locations of selected potential defects.

In accordance with an embodiment of the presently disclosed subject matter, there is further provided a system, further comprising a reference data generator configured to define the mask based on a reference image of an inspected-object reference area, to downsample a part of the reference image, and to generate the template based on a result of the downsampling.

In accordance with an aspect of the presently disclosed subject matter, there is further provided a computerized method for classifying a potential defect identified within an inspection image of an inspected object, the method comprising determining an anchor location with respect to the inspection image, based on a matching of a template and a portion of the inspection image, wherein an accuracy of the determining of the anchor location exceeds a resolution of the inspection image; based on a mask which defines different segments within an area and on the anchor location, determining a distribution of the potential defect with respect to one or more of the segments; and classifying the potential defect based on the distribution.

In accordance with an embodiment of the presently disclosed subject matter, there is yet further provided a method, wherein the inspected object is selected from a group consisting of an electronic circuit, a wafer, and a photomask.

In accordance with an embodiment of the presently disclosed subject matter, there is yet further provided a method, wherein the determining of the distribution comprises determining the distribution at an accuracy which exceeds the resolution of the inspection image.

In accordance with an embodiment of the presently disclosed subject matter, there is yet further provided a method, wherein the different segments correspond to parts of the inspected object having different physical characteristics.

In accordance with an embodiment of the presently disclosed subject matter, there is yet further provided a method, wherein the classifying comprises classifying the potential defect according to a classification in which classes correspond to defect types whose implications on an operability of the inspected object differ.

In accordance with an embodiment of the presently disclosed subject matter, there is yet further provided a method, comprising determining multiple anchor locations with respect to the inspection image, based on matching of the template and multiple portions of the inspection image; wherein accuracies of the determining of the multiple anchor locations exceed the resolution of the inspection image; based on the mask and on the multiple anchor locations, determining distributions of the potential defect with respect to one or more of the segments; and classifying the potential defect based on multiple distributions determined for it.

In accordance with an embodiment of the presently disclosed subject matter, there is yet further provided a method, further comprising selecting for further scanning potential defects which are classified into certain classes, wherein the selecting includes refraining from selecting potential defects classified into at least one class other than the certain classes; and selectively scanning, in a resolution which is higher than the resolution of the inspection image, at least one area of the inspected object which is selected based on locations of the potential defects which are selected.

In accordance with an embodiment of the presently disclosed subject matter, there is yet further provided a method, wherein the mask is determined based on a reference image of an inspected-object reference area, wherein the method further comprises generating the template, wherein the generating comprises downsampling a part of the reference image.

In accordance with an embodiment of the presently disclosed subject matter, there is yet further provided a method, wherein the reference image is generated from computer-aided design (CAD) data.

In accordance with an aspect of the presently disclosed subject matter, there is yet further provided a program storage device readable by machine, tangibly embodying a program of instructions executable by the machine to perform a method for classifying a potential defect identified within an inspection image of an inspected object, the method comprising the steps of determining an anchor location with respect to the inspection image, based on a matching of a template and a portion of the inspection image, wherein an accuracy of the determining of the anchor location exceeds a resolution of the inspection image; based on a mask which defines different segments within an area and on the anchor location, determining a distribution of the potential defect with respect to one or more of the segments; and classifying the potential defect based on the distribution.

In accordance with an embodiment of the presently disclosed subject matter, there is yet further provided a program storage device, wherein the inspected object is selected from a group consisting of an electronic circuit, a wafer, and a photomask.

In accordance with an embodiment of the presently disclosed subject matter, there is yet further provided a program storage device, wherein the determining of the distribution comprises determining the distribution at an accuracy which exceeds the resolution of the inspection image.

In accordance with an embodiment of the presently disclosed subject matter, there is yet further provided a program storage device, wherein the different segments correspond to parts of the inspected object having different physical characteristics.

In accordance with an embodiment of the presently disclosed subject matter, there is yet further provided a program storage device, wherein the classifying comprises classifying the potential defect according to a classification in which classes correspond to defect types whose implications on an operability of the inspected object differ.

In accordance with an embodiment of the presently disclosed subject matter, there is yet further provided a program storage device, comprising determining multiple anchor locations with respect to the inspection image, based on matching of the template and multiple portions of the inspection image; wherein accuracies of the determining of the multiple anchor locations exceed the resolution of the inspection image; based on the mask and on the multiple anchor locations, determining distributions of the potential defect with respect to one or more of the segments; and classifying the potential defect based on multiple distributions determined for it.

In accordance with an embodiment of the presently disclosed subject matter, there is yet further provided a program storage device, further comprising selecting for further scanning potential defects which are classified into certain classes, wherein the selecting includes refraining from selecting potential defects classified into at least one class other than the certain classes; and selectively scanning, in a resolution which is higher than the resolution of the inspection image, at least one area of the inspected object which is selected based on locations of the potential defects which are selected.

In accordance with an embodiment of the presently disclosed subject matter, there is yet further provided a program storage device, wherein the mask is determined based on a reference image of an inspected-object reference area, wherein the method further comprises generating the template, wherein the generating comprises downsampling a part of the reference image.

In accordance with an embodiment of the presently disclosed subject matter, there is yet further provided a program storage device, wherein the reference image is generated from computer-aided design (CAD) data.

BRIEF DESCRIPTION OF THE DRAWINGS

In order to understand the invention and to see how it may be carried out in practice, embodiments will now be described, by way of non-limiting example only, with reference to the accompanying drawings, in which.

Figure 1A:
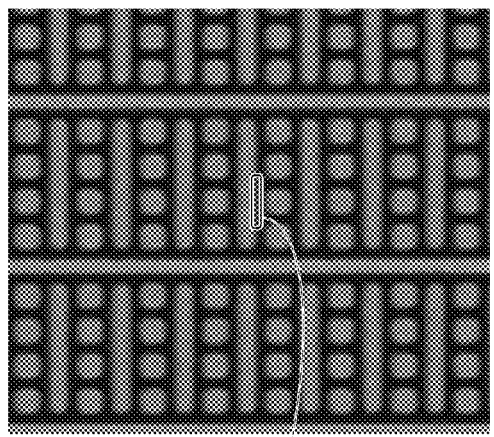
FIGS. 1A and 1B illustrate two types of defects in an electronic circuit.
Figure 1A:
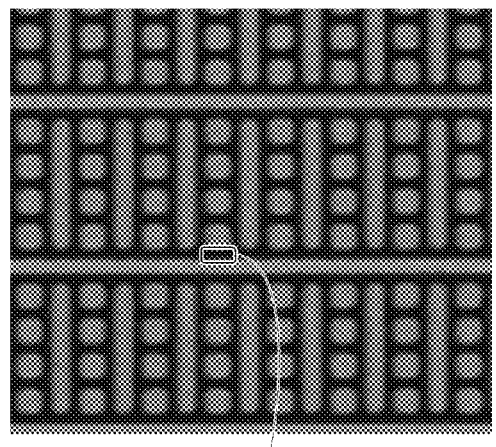
Figure 1B:
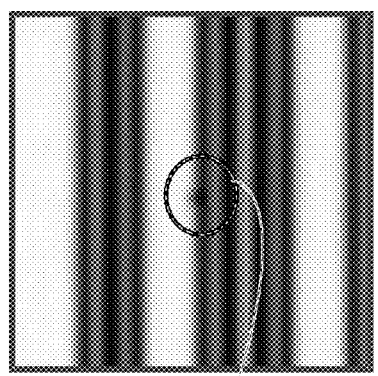
Figure 1B:
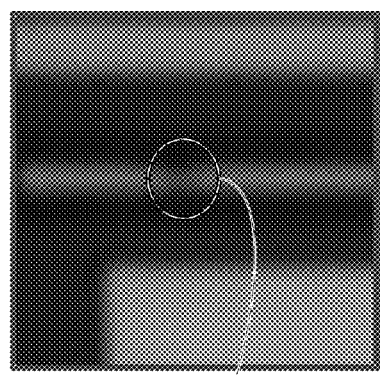

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF EMBODIMENTS

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

In the drawings and descriptions set forth, identical reference numerals indicate those components that are common to different embodiments or configurations.

Unless specifically stated otherwise, as apparent from the following discussions, it is appreciated that throughout the specification discussions utilizing terms such as processing, calculating, determining, generating, setting, selecting, or the like, include action and/or processes of a computer that manipulate and/or transform data into other data, said data represented as physical quantities, e.g. such as electronic quantities, and/or said data representing the physical objects. The term "computer" should be expansively construed to cover any kind of electronic device with data processing capabilities, including, by way of non-limiting example, a personal computer, a server, a computing system, a communication device, a processor (e.g. digital signal processor (DSP), a microcontroller, a field programmable gate array (FPGA), an application specific integrated circuit (ASIC), etc.), any other electronic computing device, and or any combination thereof.

The operations in accordance with the teachings herein may be performed by a computer specially constructed for the desired purposes or by a general purpose computer specially configured for the desired purpose by a computer program stored in a computer readable storage medium.

As used herein, the phrase "for example," "such as", "for instance" and variants thereof describe non-limiting embodiments of the presently disclosed subject matter. Reference in the specification to "one case", "some cases", "other cases" or variants thereof means that a particular feature, structure or characteristic described in connection with the embodiment(s) is included in at least one embodiment of the presently disclosed subject matter. Thus the appearance of the phrase "one case", "some cases", "other cases" or variants thereof does not necessarily refer to the same embodiment(s).

It is appreciated that certain features of the presently disclosed subject matter, which are, for clarity, described in the context of separate embodiments, may also be provided in combination in a single embodiment. Conversely, various features of the presently disclosed subject matter, which are, for brevity, described in the context of a single embodiment, may also be provided separately or in any suitable sub-combination.

In embodiments of the presently disclosed subject matter one or more stages illustrated in the figures may be executed in a different order and/or one or more groups of stages may be executed simultaneously and vice versa. The figures illustrate a general schematic of the system architecture in accordance with an embodiment of the presently disclosed subject matter. Each module in the figures can be made up of any combination of software, hardware and/or firmware that performs the functions as defined and explained herein. The modules in the figures may be centralized in one location or dispersed over more than one location.

Figure 2:
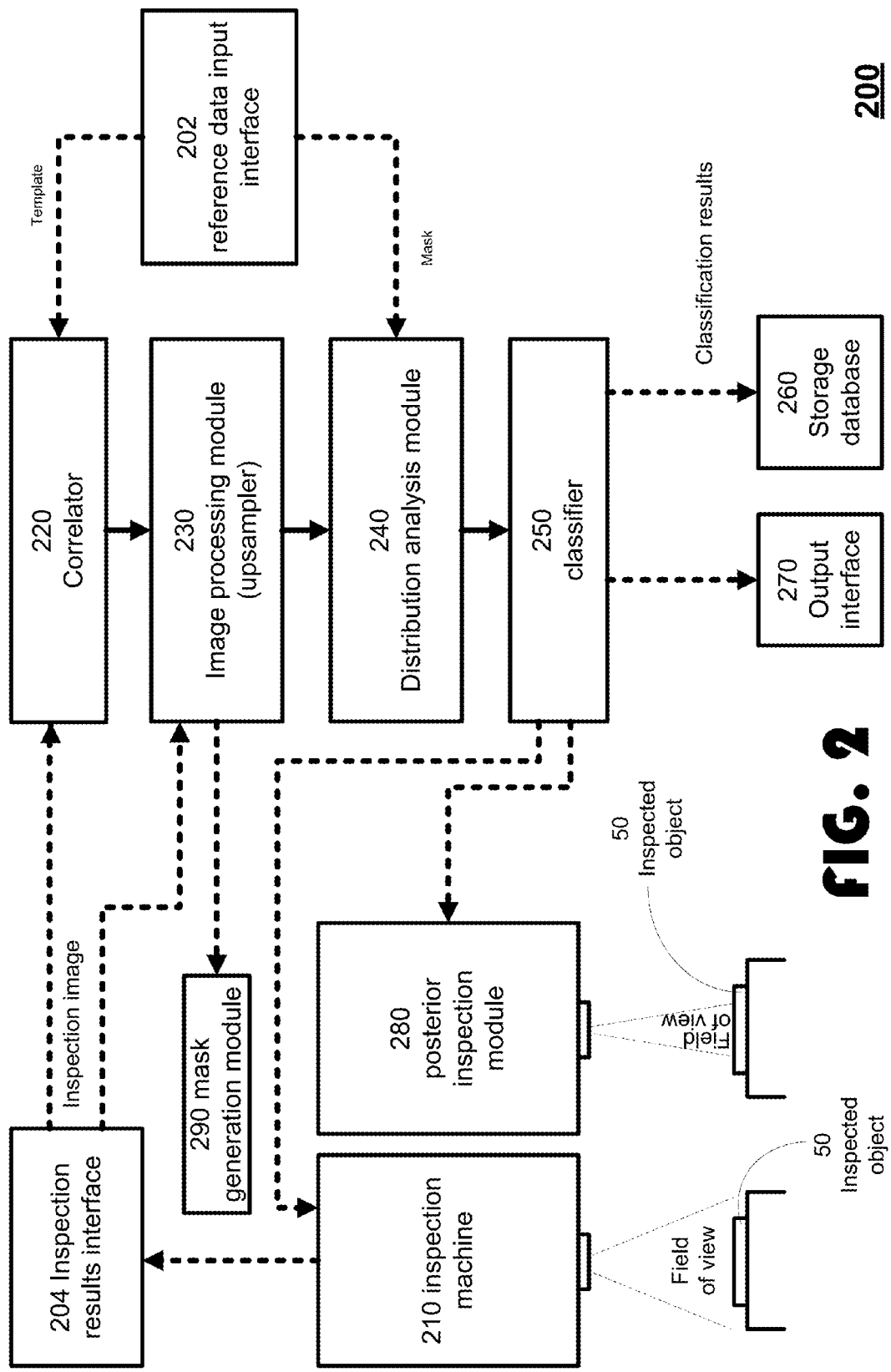
FIG. 2 is a block diagram of a potential-defect analysis system that may be used for classifying potential defects identified within an inspection image of an inspected object, according to an embodiment of the invention.

FIG. 2 is a block diagram of an analysis system 200 that may be used for classifying potential defects (or other types of identified items) which are identified within an inspection image of an inspected object 50, according to an embodiment of the invention. While not necessarily so, the inspected object may be selected from a group consisting of an electronic circuit, a wafer, and a photomask.

System 200 may obtain the inspection image in many ways. For example, system 200 may be combined with an inspection machine 210 that is used to inspect the wafer or other types of inspected object (e.g. during different stages of manufacturing thereof). In another implementation system 200 may be connected to such an inspection machine, or the inspection image may be transmitted by an off-line device connected to only one of the machines at a time. Also, system 200 may be an inspection machine into which some or all of the modifications and/or features discussed below have been integrated.

As will be discussed below in more detail, one or more of the components of system 200 may be used to classify potential defects that were detected in a scanned image of the wafer. This determined classification may later be used in the manufacturing the wafer, and/or in later stages of inspection of the wafer. Some of the ways in which system 200 may operate will become clearer when viewed in the light of method 500 discussed below.

System 200 includes pattern matcher 220 which is configured to determine an anchor location with respect to the inspection image, based on a matching of a template and a portion of the inspection image. For example, pattern matcher 220 may be configured to compute a correlation between the template and different portions of the inspection image, and to define the anchor location based on the portion whose correlation with the template is the highest. Optionally, pattern matcher 220 may be configured to select within the inspection image a cell-area of a predetermined cell-size (e.g. selecting the area with the highest correlation, based on results of the correlation). It should be noted that while not necessarily so, pattern matcher 220 may be configured to determine the anchor location at an accuracy which exceeds a resolution of the inspection image. Examples of ways in which pattern matcher 220 may operate are discussed in further detail in relation to stages 530 and 540 of method 500.

The template may be received from reference data input interface 202, or may be generated by a component of system 200, such as image processing module 230. The inspection image may be received via inspection results interface 204, or may be acquired by imaging system 210 (also denoted "inspection machine").

Optionally, system 200 may include an image processing module 230 that is configured to upsample the area 110 to a resolution higher than the resolution of the inspection image. Examples of ways in which image processing module 230 may operate are discussed in further detail in relation to stage 550 of method 500.

Distribution analysis module 240 is configured to determine, based on the anchor location and on a mask which defines different segments within an area, a distribution of the identified item (e.g. the potential defect) with respect to one or more of the segments of a mask. Examples of ways in which distribution analysis module 240 may operate are discussed in further detail in relation to stage 560 of method 500.

As will be discussed below in more detail, according to an embodiment of the invention, distribution analysis module 240 may be configured to determine the distribution in a sub-pixel level with respect to the resolution of the mask.

Classifier 250 of system 200 is configured to classify the identified item (e.g. the potential defect) based on the distribution determined for it by distribution analysis module 240 (and possibly also based on classification rules, e.g. as discussed below). It should be noted that classifier 250 may use additional factors pertaining to the potential defect during its classification, such as grey level, size, shape, etc.

System 200 may include a tangible storage 260 (e.g. a hard-drive disk, a flash drive, etc.) for storing the classification (or part thereof—e.g. only the defects which were classified as noteworthy) to a tangible storage. System 200 may also include an output interface 270 for transmitting the classification (or part thereof) to an external system (e.g. over cable connection or over wireless connection), wherein that external system may in turn act based on the classification.

System 200 may also include an inspection module, which may be the aforementioned inspection machine 210 which provides the aforementioned inspection image by scanning of the inspected objects such as the wafers, and may alternatively be posterior inspection module 280 that is configured to inspect the wafer (or other inspected object) in higher resolution than that of the inspection image. This inspection module is configured to selectively scan, in a resolution higher than the resolution of the inspection image, areas of the inspected object which are selected based on the locations of identified items (e.g. potential defects) which are classified into certain classes but not into at least one of the other classes (i.e. refraining from selecting potential defects classified into at least one class other than the certain classes). The field of view of posterior inspection module 280 may be narrower than that of inspection machine 210, but this is not necessarily so.

In such a case, the areas selected for further scanning may be selected based on the locations of potential defects which are classified into certain classes but not into at least one of the other classes. For example, the scanning in the higher resolution may be carried out around the locations of the possible defects classified as "short gate", but not around the locations of the possible defects classified as "edge roughness".

It should be noted that inspection machine 210 and/or posterior inspection module 280, if implemented, may be implemented as inspection machines of various types, such as optical imaging machines, electron beam inspection machines, radars, LIDARs and so on.

Generally, identifying defects in a wafer (or in another inspected object) may be implemented using different techniques, among which are optical inspection and electron beam inspection. Utilization of system 200 may facilitate the use of more than a single inspection technique. For example, an initial inspection of the wafer is firstly carried out relatively quickly and in a coarse manner by inspection system 200 (e.g. using an optical inspection or an electron beam inspection set for coarse and fast inspection). Later, some of the potential defects found in the initial inspection (selected based on the classification results of classifier 250) are then studied again using a relatively slower but more exact inspection. Such posterior scanning may be executed either in another mode of inspection machine 210, or in a different posterior inspection module 280 (in a process also referred to as "reviewing", e.g. by DRSEM—Defect Review Scanning Electron Microscope).

Referring to the mask mentioned above, optionally the mask may define segments of multiple types, wherein the number of types is smaller than the number of segments. In such implementations, distribution analysis module 240 may be configured to determine a type-based distribution of the potential defect between one or more of the types; and classifier 250 may be configured to classify the potential defect based on the type-based distribution. However, for simplicity of explanation, it will be assumed that each segment is handled independently of other segments.

While not necessarily so, the different segments may correspond to parts of the inspected object having different physical characteristics, such as the material they are made from, their reflective value, their electrical conductance, and so on. As discussed in greater detail below, classifier 250 may be configured to classify the potential defect (or other identified item) according to a classification, in which classes that correspond to defect types, whose implications on operability of the inspected object, differ.

In some implementations, pattern matcher 220 may be configured to determine multiple anchor locations with respect to the inspection image, based on matching of the template and multiple portions of the inspection image. Likewise, pattern matcher 220 may optionally be configured to select within the inspection image multiple cell-areas of the predetermined cell-size, based on correlation of the template to multiple different portions of the inspection image. As in the case of selecting a single anchor location, the accuracies of the determining of the multiple anchor locations may exceed the resolution of the inspection image.

Distribution analysis module 240 may be configured in such implementation to determine, based on the mask and on the multiple anchor locations, distributions of the potential defect with respect to at least one segment of the mask. Also, classifier 250 may be configured to classify a single potential defect based on multiple distributions determined for that single potential defect by distribution analysis module 240.

Referring to the example and terminology of FIG. 5 which is discussed below, since a single identified item may be included in two or more cell-areas processed, according to an embodiment of the invention classifier 250 may be configured to classify the potential defect based on distributions determined for it in two or more different cell-areas.

Instead of receiving the mask and the template from an external system via reference data input interface 202, system 200 may include a reference data generator (not illustrated) which is configured to define the mask based on a reference image of an inspected-object reference area. A reference data generator of system 200 may be configured to downsample a part of the reference image, and to generate the template based on a result of the downsampling. While the template may have a lower resolution than the reference image and/or the inspection image, it is noted that image processing techniques other than a simple downsampling may also be implemented in the generating of the template, in addition to or instead of the downsampling. The reference data generator may be configured to generate the reference-image from computer-aided design (CAD) data, or to use a scanning image as a reference.

As aforementioned, some of the ways in which system 200 and its component may operate are discussed in greater detail with respect to method 500.

System 200 may be implemented on a computer (such as a PC), e.g. the computer which implements the overall classification (Image Based Attributing, IBA) of the runtime inspection results, but this is not necessarily so. Each of the modules or components of system 200 may be implemented in software, hardware, firmware, or any combination thereof. Additionally, system 200 may also include other components that are not illustrated, and whose inclusion will be apparent to a person who is of skill in the art—e.g. a power source, a display, etc.

Figure 3:
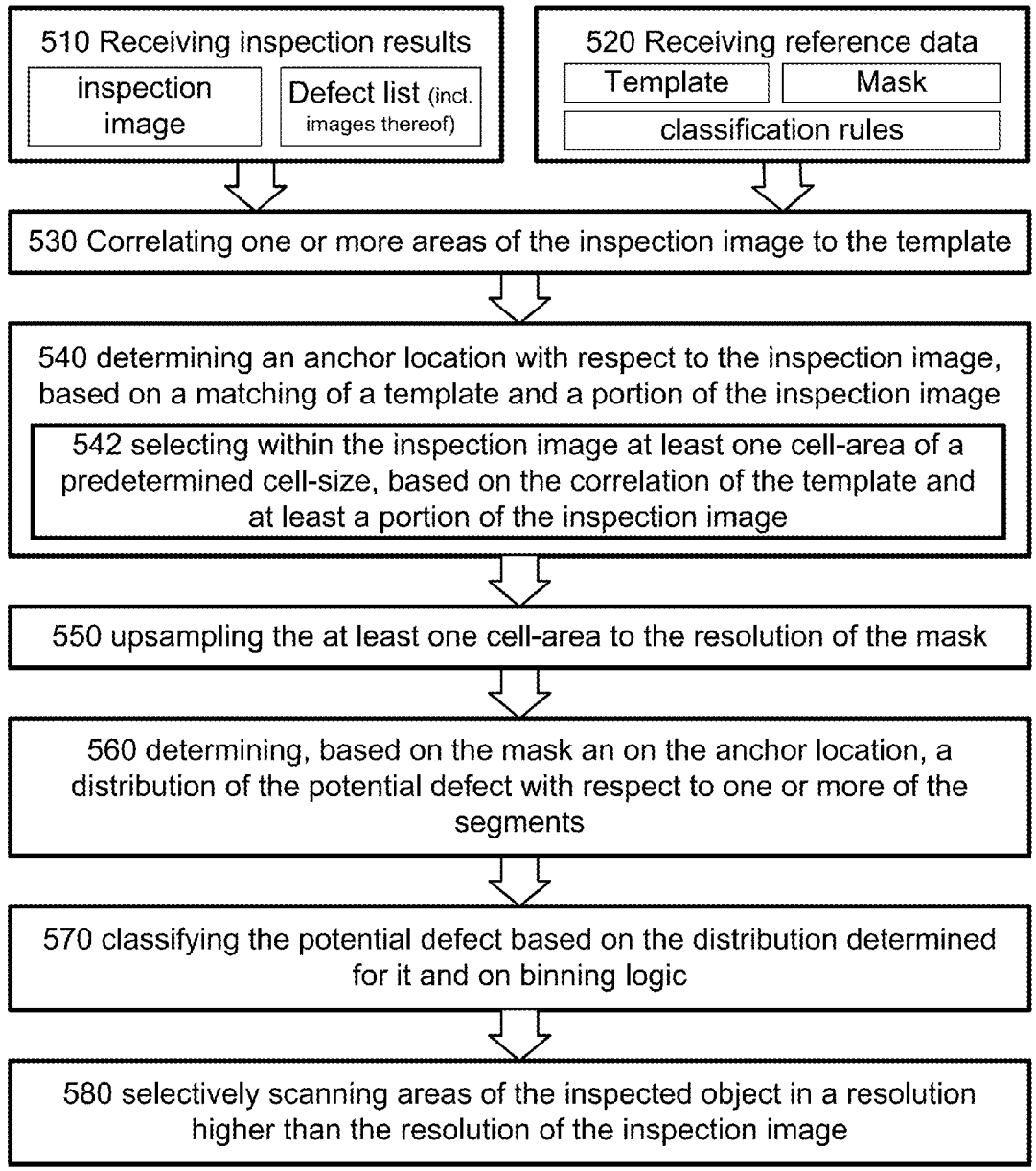
FIG. 3 is a flow chart of a computerized method for classifying an item identified within an inspection image of an inspected object, according to an embodiment of the invention.

FIG. 3 is a flow chart of computerized method 500 for classifying an item identified within an inspection image of an inspected object, according to an embodiment of the invention. Referring to the examples set forth in the previous drawings, method 500 may be carried out by system 200. Different embodiments of system 200 may implement the various disclosed variations of method 500 even if not explicitly elaborated. Likewise, different embodiments of method 500 may include stages whose execution fulfills the various disclosed variations of system 200, even if succinctness and clarity of description did not necessitate such repetition.

Method 500 may be implemented for various types of inspected objects, from a very minute scale (e.g. millimetric or nanoscale objects) to larger objects such as geographical area imaged from an airplane or from a satellite. The item identified may be a specific item or a group thereof (e.g. looking for tanks in an areal image), but may also be, for example, a deviation from an expected pattern (such as a hole in a textile fabric, or a potential manufacturing defect in a wafer).

In order to clarify the disclosure, different stages of method 500 would be exemplified using a revised example of an inspected object which is selected from a group consisting of an electronic circuit, a wafer, and a photomask (a partially transparent plate which may be used for the manufacturing of electronic circuits or other objects in a process implementing transmitting light through such a photomask, such as photolithography). The one or more items identified within the inspection image would be exemplified in such cases using the example of potential defects. A person who is of ordinary skill in the art would nevertheless understand that this is merely but one example, and that many other types of inspected objects and items identified within inspection images thereof (such as the examples provided above) may be implemented.

Method 500 may include stage 510 of receiving inspection results which includes the inspection image in which at least part of the inspected object is imaged. Referring to the examples set forth in the previous drawings, stage 510 may be carried out by an inspection result interface such as inspection results interface 204 of system 200.

The inspection results may further include item identification information identifying one or more items which were identified within the inspection image. The item identification image may include one or more of the following:
  a. Location information of each of the one or more items (e.g. indication of one or more pixels in the inspection image which correspond to the item, or even indication in a sub-pixel accuracy);
  b. Size information, indicating size of the item (e.g. indicated in pixels);
  c. Type information, identifying initial classification of the item;
  d. Small image excerpts of the inspection image, each of which includes one or more of the items;
  e. Grade of the item in one or more grading systems (e.g. indication of the likelihood of defectiveness of the indicated potential defect).

Clearly, the item identification information may include additional information. In an example in which the items are potential defects identified in an inspection image of a wafer, the item identification information may also be referred to as a defect list.

Clearly, the receiving of the inspection image may be replaced by a stage of capturing (or otherwise generating) the inspection image. For example, this may be implemented by optical photography, by electron beam inspection, by laser beam inspection, and so on. Likewise, item identification information may not only be obtained by receiving same from an external entity, but may also be obtained by image-processing the inspection image, and generating item identification information based on the results of the image processing.

Method 500 may also include stage 520 which includes receiving reference data which includes at least one of the following data entities, whose content and use will be described below: template, mask, and classification rules. In another implementation, one or more of those data entities may be created as part of the method. Creation of such data entities is discussed in relation to method 600, which may be implemented as part of method 500, or independently thereof. Referring to the examples set forth in the previous drawings, stage 520 may be carried out by a reference data input interface such as reference data input interface 202 of system 200. The template, mask and the classification rules may be user defined, machine defined, and so on.

The classification rules will be discussed in due course, as part of the discussion of their utilization in method 500. The template and mask data entities will be introduced with reference to FIG. 4.

Figure 4:
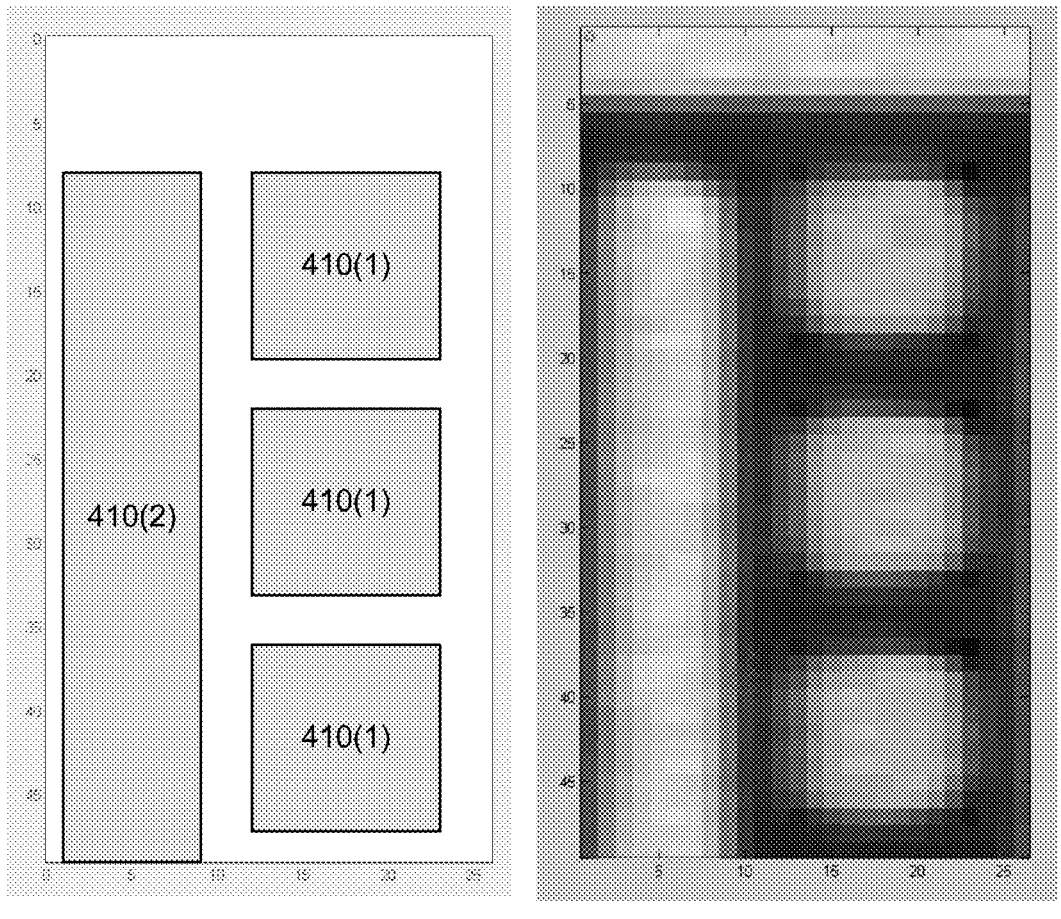
FIG. 4 illustrates a template and a representation of a mask, according to an embodiment of the invention.

FIG. 4 illustrates a template 300 and a representation of a mask 400, according to an embodiment of the invention. According to such an embodiment of the invention, template 300 is an image. The template image may be an actual image of a part of the inspected object, or a similar image. For example, the image data of template 300 may be obtained by actually imaging a part of the inspected object (or a similar reference object, e.g. as discussed below). In other embodiments the image data of template 300 may be obtained by processing design data (e.g. CAD data). As will be discussed below, the image data of the template may be obtained by downsampling (i.e. reducing the spatial resolution of) at least a part of an original image of higher resolution. The resolution of the received template may be the same as the resolution of the runtime inspection image, but this is not necessarily so.

The mask (represented by the region denoted 400) defines different segments 410 within a predefined area (also referred to as "cell-sized area". While conversion of units may be applied, the term "size" in the context of the cell-sized area pertains to coordinates of the inspection plane, such as the plane of the inspected layer of the wafer when the later is inspected).

The different segments 410 may be of the same or different sizes, and of the same or different shapes. While the segments 410 are illustrated as rectangular, this is not necessarily so, and segments 410 of other shapes may also be implemented. The various segments 410 may cover the entire area of the mask, but this is not necessarily so.

The size of the mask may be defined in response to external data, or otherwise. For example, if the inspected object includes a repeating pattern (e.g. as exemplified in FIG. 6), the size of the mask may correspond to the size of the repeating area (denoted 180 in FIG. 6), or to a part thereof.

Optionally, the segments 410 defined by the mask 400 may be of multiple types (e.g. wherein the number of types is smaller than the number of segments). This is exemplified in that the three segments denoted 410(1) are of the same type. Each of the segments 410 (or of the different types of segments) may correspond to parts of the inspected object that have different physical characteristics. For example, different levels of electrical conductivity in the inspected object may correspond to different types of segments.

The various segments 410 (or the different types of segments) may be defined according to the type (or types) of items whose classification is achieved by method 500. For example, if method 500 is used for classification of potential defects, different segments 410 (or types thereof) may correspond to different parts of the inspected object (e.g. wafer, electronic circuit or photomask) which have different susceptibility to defects, and/or different likelihood to have different types of defects. It should be noted that in some implementations, a single segment may cover areas which are not connected to each other. For example, in such an implementation, all of the segments 410(1) may be considered as a single segment, and not only as several segments of the same type.

The mask may be stored in different formats. For example, it may be stored as an image (in which different colors correspond to different types of segments), as a table (e.g. denoted starting point, dimensions, and possibly type for each of the segments), in vectorial format, and so on.

In FIG. 4, the template 300 and the mask represented (denoted 400) both correspond to a similarly sized area of the inspected object (albeit possibly having different resolutions). However, in other implementations—e.g. as exemplified in FIG. 5—the physical areas to which the template and the mask pertain may be different from each other. In such a case, one of those corresponding areas may be included within the other (as exemplified in FIG. 5), partly overlapping, and even non-overlapping.

Reverting to FIG. 3, method 500 may include stage 530 of correlating the template and at least a portion of the inspection image. While the template is not necessarily identical to any of the correlated portions of the inspection image, its correlation to some of the portions would be higher than its correlation to others. For example, the correlation of the template to one of the portions may be relatively high, and at least higher than portions of the inspection image which are slightly shifted with respect to said portion. Referring to the examples set forth in the previous drawings, stage 530 may be carried out by a pattern matcher such as pattern matcher 220 of system 200.

It should be noted that the correlation does not necessarily conform to the pixels of the inspection image. It is noted that the correlation may be implemented in sub-pixel accuracy (e.g. in accuracies of thousandth of a mask pixel). As can be seen in the example of FIG. 5, area 130, which is assumed in the example to be the one best correlating the template, is not located on the grid representing the pixels of the inspection image 100, but is rather located (hence determined) in a sub-pixel resolution. The correlating of stage 530 may be carried out based on the defect list (e.g. only in areas of the wafer in which potential defects were detected) or regardless thereof.

Stage 540 of method 500 includes determining an anchor location with respect to the inspection image, based on a matching of a template and a portion of the inspection image. Referring to the examples set forth in the previous drawings, stage 540 may be carried out by a pattern matcher such as pattern matcher 220. The anchor location may be, for example, the location of anchor 120 (which may be a dimensionless point or another kind of an anchor). It should be noted that while the matching of the template and the portion of the image (e.g. area 130 illustrated in FIG. 5) may be accomplished by a correlation (such as in stage 530), in other implementations other matching techniques may be implemented (such as pattern detection, and so on). While not necessarily so, in some implementations an accuracy of the determining of the anchor location exceeds a resolution of the inspection image.

Optionally, method 500 may include stage 542, which includes selecting within the inspection image a cell-area of a predetermined cell-size, wherein the selecting is based on the correlation of the template and at least a portion of the inspection image (or other type of matching between the two). In a way, if a geometrical relationship between the anchor location and the cell-sized area is known in advance (e.g. arrow 122 of FIG. 5, as well as the size of area 110), the selecting of the cell-area in stage 542 may be a direct by-product of the selecting of the anchor location in stage 540.

While conversion of units may be applied, the term "size" in the context of the cell-area pertains to coordinates of the inspection plane (e.g. the plane of the inspected layer of the wafer when the latter is inspected). While the cell-size may be identical to the area-size defined by the mask, this is not necessarily so, and the mask may define the segments within a larger area, that includes the aforementioned cell-sized area. Referring to the examples set forth in the previous drawings, stage 540 may be carried out by a correlator such as pattern matcher 220.

It should be noted that if the resolution of the mask is higher than that of the cell-area, then the two areas would have different pixel size, even if pertaining to similar sized areas in the inspection plane. Referring to the size of the template in the coordinates of the inspection plane, the size of the cell-area may be smaller, similar, or larger than the area of the template.

In some implementations of the invention, a decision rule may be implemented prior to execution of stage 540, according to which if no area of the inspection image may be matched to the template in a sufficiently successful manner, the method is terminated. For example, if no portion of the inspection image is found to have a correlation score which exceeds a predetermined threshold, an anchor location is not necessarily determined. While one possible result of stage 530 (or another stage of matching the template to an area of the inspection image) is singling out of at least one portion of the inspection image based on its correlation to the template, another possible result is that no area is found to be matching.

Figure 5:
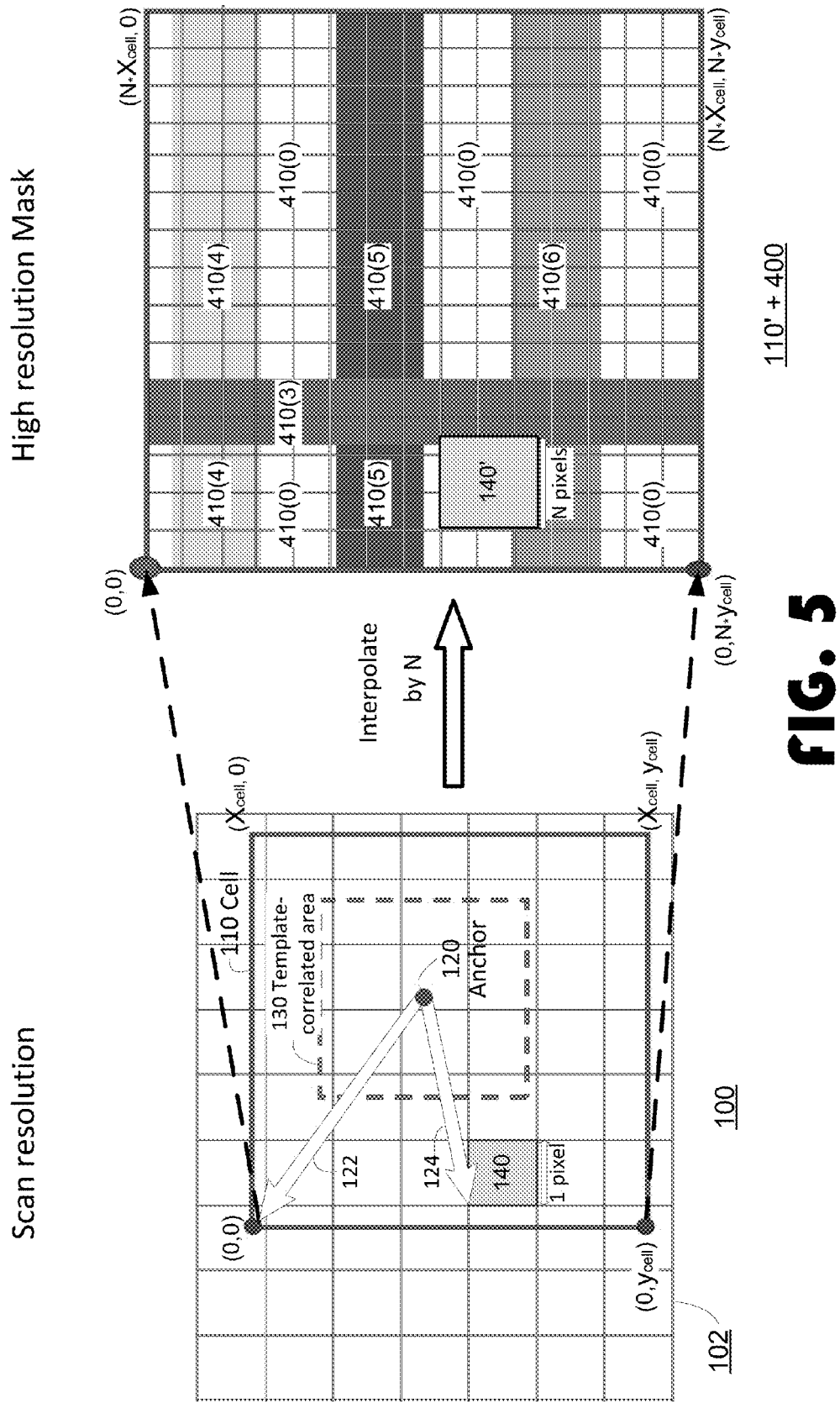
FIG. 5 illustrates relationships between entities used in the classification, according to an embodiment of the invention.

Reverting to stage 540, optionally, an anchor may be defined for any one of those singled out portions of the inspection image (referring to the example of FIG. 5, an anchor 120 may be defined within or otherwise with respect to area 130 selected within inspection image 100). If stage 542 is implemented, the selecting of that stage may include selecting the portion (or portions) of the inspection image singled out in stage 530, but may also include selecting another area of the inspection image. Referring again to the example of FIG. 5, the area 110 selected in stage 542 is larger than the area 130 selected in stage 530. Area 110 (also referred to as "cell-area" 110) may be defined with respect to anchor 120 which is determined in stage 540 (for example it may be defined with respect to area 130, which was singled out of the inspection image, based on the matching).

Figure 6:
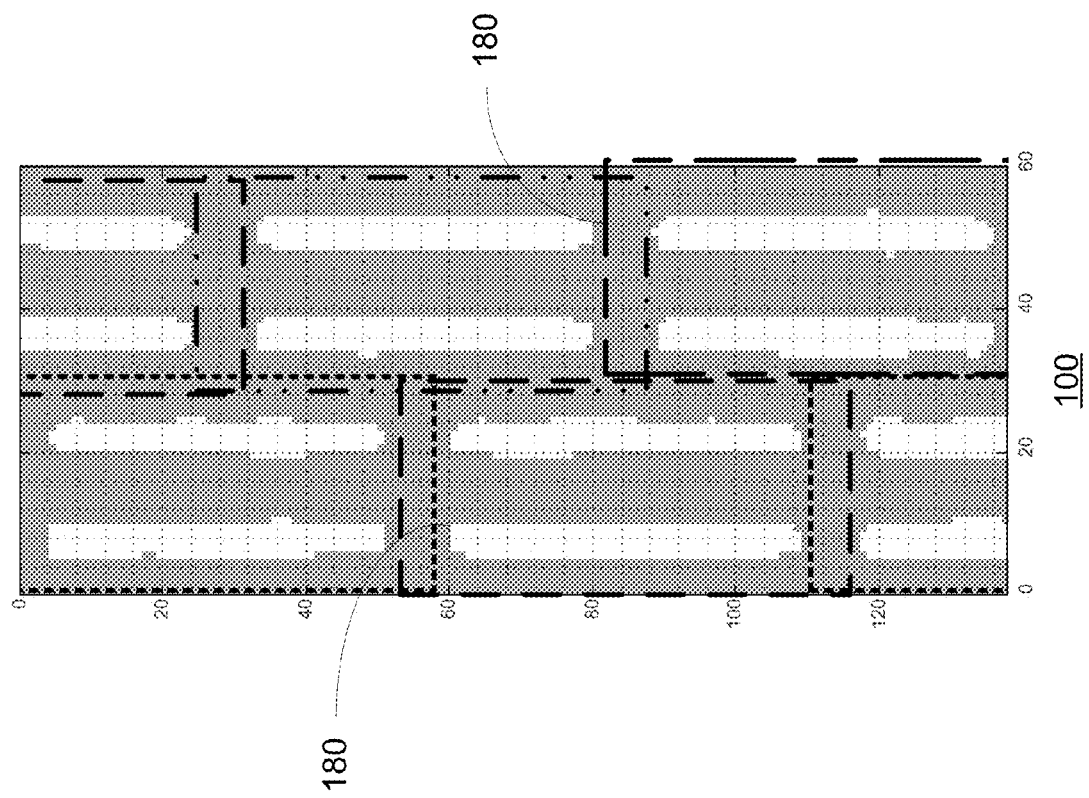
FIG. 6 illustrates a repeating pattern in an inspection image, according to an embodiment of the invention.

As mentioned above, the inspected object may include a repeating pattern (e.g. as exemplified in FIG. 6). If the template corresponds to a part (or all) of the area that is repeated in the pattern, many similar portions of the inspection image may be matched to the template (e.g. correlated, as in stage 530), and many anchor locations may be determined correspondingly in stage 540.

For example, the inspected object imaged in the inspection image 100 of FIG. 6 includes a repeating pattern that includes multiple occurrences of a pair of vertical lines. While those multiple areas are not identical, each matching of the template to one of those areas may nevertheless result in a defining of a separate anchor location in stage 540 (e.g. based on a correlation of different portions of the inspection image to a template, which is not shown).

Multiple portions of the inspection image that are similar to the template may yield determination of multiple anchor location (and possibly also to a selection of multiple cell-sized areas) even if the similar portions do not form a recurring pattern. All the more so, in some implementations multiple templates may be implemented (e.g. which correspond to different recurring patterns in the wafer), wherein multiple anchor location may be determined in stage 540 based on matching of various areas of the inspection image to multiple templates. In such a case, masks of different sizes may be used for such areas. If multiple anchor locations areas are determined in stage 540, some or all of the following stages of method 500 may be repeated for some or all of those multiple anchor locations.

As aforementioned, the resolution of the mask may be different, and particularly may be higher, than that of the inspection image. That is, the segments defined in the area of the mask may be defined in a resolution higher than that of the inspection image, and particularly—a resolution higher than that of the one or more selected cell-areas, if selected at optional stage 542.

In such a case, method 500 may optionally include stage 550 of upsampling the cell-area of stage 542 to a resolution higher than the resolution of the inspection image. Especially, stage 550 may include upsampling the cell-area to the resolution of the mask. Referring to the examples set forth in the previous drawings, stage 550 may be carried out by an image processing module such as image processing module 230 of system 200.

Referring to the example of FIG. 5, area 110 (hereinafter also simply referred to as "cell" or as "area 110") is an $X_{cell}$ by $Y_{cell}$ pixels sized area. It can be seen that while $X_{cell}$ and $Y_{cell}$ may be an integer, the location of the area 110 does not have to read exactly on the grid of pixels (denoted 102) of the inspection image 100. For example, the best matching between the template and the inspection image may be achieved for an area that is defined in non-integer pixel coordinates. In an additional example, the distance between the location of anchor 120 and the corresponding area 110 may be defined in non-integer pixel coordinates.

On the right side of FIG. 5, an upsampled version of area 110 is illustrated (denoted 110'), overlapped with a representation of the mask 400. As can be seen, in the resolution of the inspection image the size of the area 110 (also referred to as "cell") is 6 by 6 pixels. The size of the upsampled version thereof is 15 by 15 pixels. In the illustrated example, the upsampling of the area 110 into area 110' including increasing the resolution by a factor of N=2.5. It is again noted that while upsampling of a selected cell area may be implemented in some implementations of the invention, it is not necessarily so. As noted above, in some implementations no such cell-area is selected or defined.

If implemented, the upsampling may include a simple linear interpolation. In other implementations, other types of interpolation techniques may be implemented—such as bicubic interpolation, bilinear interpolation, nearest-neighbor interpolation, and so on.

By way of illustration, highlighted pixel 140 of the inspection image corresponds to an N by N pixels area, denoted 140', in mask-resolution (if indeed implemented as a raster image), in an example in which a linear interpolation is implemented.

Highlighted pixel 140 may represent, for example, a location of a potential defect detected during an analysis of the inspection image. It should be noted, however, that potential defects may also possibly be defined as larger or as smaller than a single pixel.

The different segments 410 of the mask are illustrated as defined in a sub-pixel resolution. This may be implemented for example in a vectorial representation of the mask. It should be noted that in some implementations, segments 410 of the mask may be defined only in resolution of whole pixels—e.g. if the mask is defined as a raster image. Different segments of the mask are enumerated in FIG. 5 as 410(3), 410(4), 410(5), and 410(6). The areas denoted 410(0) may be defined in the mask as segments (thereby having the segments covering the entire area), or not be defined at all (thereby having the segments covering the area only partially).

Reverting to FIG. 3, method 500 continues with stage 560 of determining, based on the mask (which, as aforementioned, defines different segments within an area) and on the anchor location, as well as distribution of the identified item (e.g. the potential defect) with respect to one or more of the segments. Referring to the examples set forth in the previous drawings, stage 560 may be carried out by a distribution analysis module such as distribution analysis module 240 of system 200.

Referring to the example of FIG. 5, it is noted that a relationship between the segments of the mask and the identified item may be facilitated by knowledge of a relationship between the location of anchor 120 and at least one reference point of the mask (this is illustrated by arrow 122, and may be part of the reference data) and knowledge of a relationship between the location of anchor 120 and at least one reference point on the identified item (this is illustrated by arrow 124, and may be determined since both anchor location and the location of the identified item may be defined in coordinates of the inspection image 100).

It can be seen that the area 140' (which is an enlarged analogue of pixel 140 of the inspection image) is distributed between segments 410(0), 410(3) and 410(6) of the mask. As aforementioned, the size of the potential defect (or other item) may also be more or less than one pixel. As aforementioned, the identified item (e.g. the potential defect in the wafer) may be associated with location information and possibly also size information and/or grade, as obtained with the item identification information.

It should be noted that the determining of the distribution may include determining the distribution at an accuracy which exceeds the resolution of the template, of the inspection image, and/or the accuracy in which the mask is defined. This enables, inter alia, to provide classification based on high resolution rules, while not requiring an increase of the resolution of the scanning.

Figure 7:
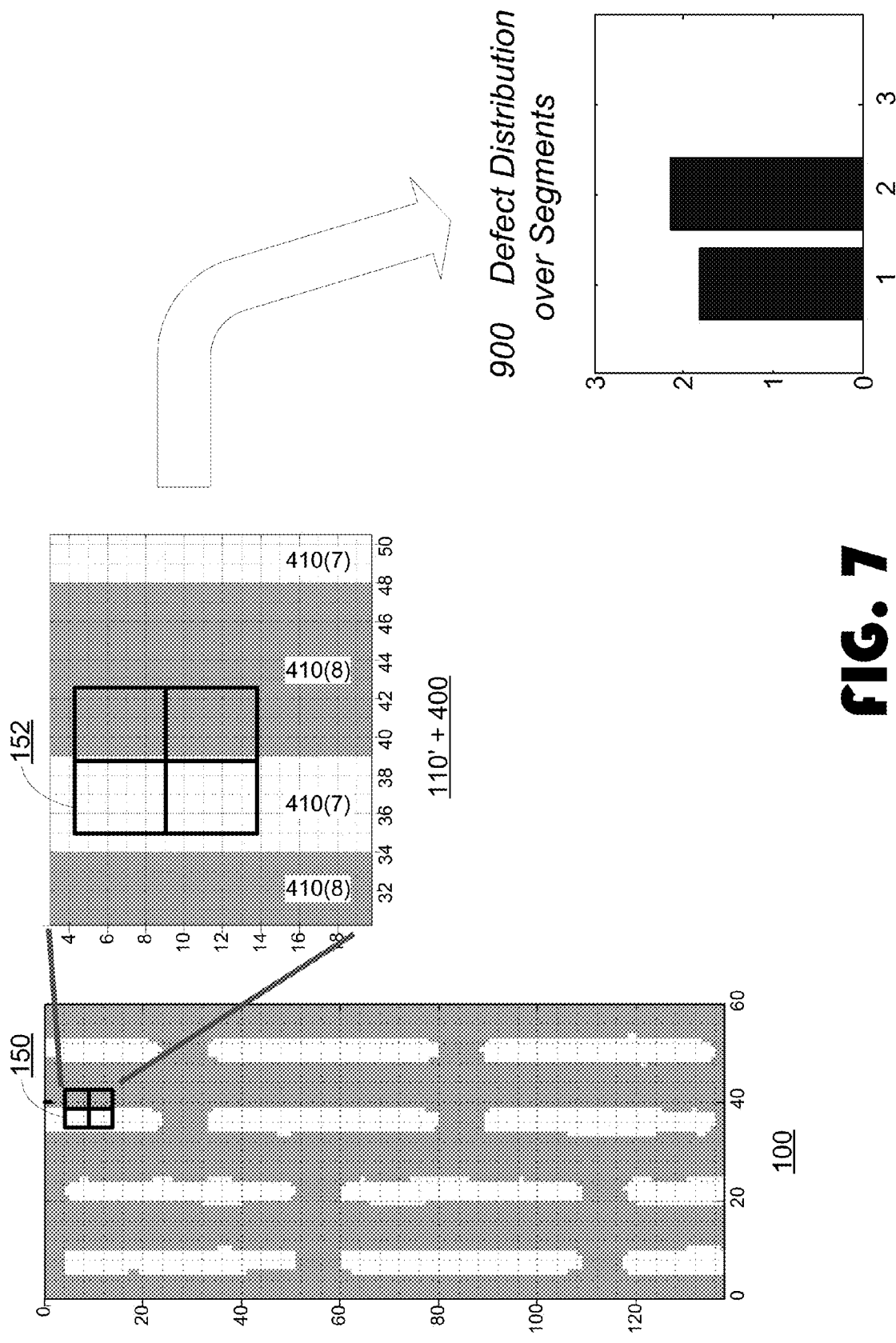
FIG. 7 illustrates distribution of a potential defect identified in an inspection image of a wafer between multiple segments defined by a mask, according to an embodiment of the invention.

In the example of FIG. 7, the size of the item (e.g. the potential defect) as identified in the inspection image is not a single pixel (as in the example of FIG. 5), but rather four pixels, illustrated by area 150 in FIG. 7. The upsampled analogue of area 150 is area 152. Area 152 is illustrated as divided into four quarters, but this is done for illustratory reasons only, and, as aforementioned, the determining of the distribution is done in a higher resolution.

As can be seen, slightly more than half of area 152 overlaps with segment 410(7), and slightly less than half overlaps segment 410(8). This is reflected by the determined distribution (denoted 900) in which segment type 1 (which corresponds to segments 410(8)) receives a score of just under 2, and segment type 2 (which corresponds to segments 410(7)) receives a score of just over 2. In the given example, the scores in the distribution are given in units equal to the original pixels of the inspection image, but a person who is of skill in the art would understand that any other method of determining the distribution may be implemented. For example, the distribution may be determined in percents, in pixels (usually a fractional quantity), in nanometers, and so on, wherein such definition would usually be similar to that in which the classification logic was defined.

It is noted that while the area that corresponds to the identified item may be distributed between multiple segments of the mask, this is not necessarily the case, and the entire area may correspond to a single segment of the mask.

As aforementioned, the mask may define segments of multiple types (e.g. segments 410(7) and segments 410(8)), wherein the number of types is smaller than the number of segments. In such a case the determining of the distribution may include determining a type-based distribution of the potential defect between one or more of the types—e.g. as exemplified in FIG. 7. The classifying of stage 570 in such a case would be based on the type-based distribution.

Reverting to FIG. 3, method 500 further includes stage 570 of classifying the identified item (e.g. the potential defect) based on the distribution determined for it. The classifying of stage 570 may be further based on the classification rules (which may also be referred to as "binning rules", "binning logic" and "classification logic"). Referring to the examples set forth in the previous drawings, stage 570 may be carried out by a classifier such as classifier 250 of system 200.

The classification rules may indicate to which class an identified item (e.g. a potential defect) should be classified, based on the distribution for it. By way of example, referring to the illustration of FIG. 7, the classification rules may indicate that a potential defect identified in the inspection image of the wafer should be classified as insignificant if less than 50% of it corresponds to segment 410(7), but classified as significant if more than 50% of it corresponds to this segment.

Table 1 is an example of binning logic, according to an embodiment of the invention. The final classification is shown in the Class Name column, and the rules by which this classification is selected are represented by the symbols (1, 0, X) in the middle five columns "1" represents that the segment must be found, "X" represents that the segment may or may not be found, and "0" represents that the segment must not be found. The priority indicates that, in implementation, if the conditions for two or more rules are fulfilled, the rule with the lower priority index would be selected. For example, fulfillment of the conditions for selection of rule 2 would also qualify for rule 3. However, since rule 2 has a lower priority index, it will be selected over rule 3.

TABLE 1

| Priority | Seg-ment 1 | Seg-ment 2 | Seg-ment 3 | Seg-ment 4 | Other | Class name |
|---|---|---|---|---|---|---|
| 1 | 0 | 0 | 0 | 1 | 0 | 4 only |
| 2 | 0 | 0 | 0 | 1 | 1 | 4 and other |
| 3 | 1 | 1 | 0 | X | X | DOI 1 |
| 4 | 1 | 1 | 1 | X | X | DOI 2 |

The classification of stage 570 may be just a part of a larger classification process, which may depend on other parameters as well. For example, the classification of the identified item (e.g. the potential defect of the wafer) may also depend on its size, color, bright field/dark field, etc. This classification may be implemented by combining method 500 for classification in a more general binning application, such as those used for binning of potential defects in wafer inspection in prior art machines.

As aforementioned, the different types of the segments may correspond to parts of the inspected object which have different physical characteristics (e.g. electrical characteristics, different internal construction, made of different material, and so on). In such a case, the classifying may include classifying the potential defect into classes that correspond to defect types which have electrically different implications on electrical operability of the inspected object. This may include, for example, classifying potential defects in a wafer or a photomask into "edge roughness" defects versus "short gate" defects.

As indicated above, method 500 may include determining within the inspection image multiple anchor locations (and possibly also multiple cell-areas of the predetermined cell-size), based on matching of the template to multiple different portions of the inspection image (possibly only in areas of the inspection image in which defects were detected, but not necessarily so). In such a case, the stages of determining of a distribution and classifying (as well as potentially other stages of method 500) may be repeated for the multiple cell-areas.

Reverting to the determined distribution, it is noted that since the cell-areas may partly overlap each other (e.g. in a repeating pattern, such as exemplified in FIG. 6), a single item (e.g. potential defect) may be processed for two instances of the mask (in stage 560), and its defect distribution will be different in each instance. The classification rules in such a case may include instructions for how to proceed in such situations (e.g. prefer the worst-case scenario, average the results, have the potential defect appear twice in the results, etc.).

Generally, according to an embodiment of the invention, the classifying may include classifying the potential defect based on two or more distributions determined, based on two or more anchor locations.

Once the item (or items) has been classified, actions may be continued based on the classification. Method 500 may conclude with storing the classification (or part thereof—e.g. only the defects which were classified as noteworthy) to a tangible storage and/or with transmitting the classification (or part thereof) to an external system which, in turn, may act based on the classification.

However, method 500 may also continue with other actions that are based on the classification. For example, method 500 may continue with stage 580 of selectively scanning areas of the inspected object in a resolution higher than the resolution of the inspection image. In such a case, the areas selected for further scanning may be selected based on the locations of potential defects which are classified into certain classes but not into at least one of the other classes. For example, the scanning in the higher resolution may be carried out around the locations of the possible defects classified as "short gate", but not around the locations of the possible defects classified as "edge roughness".

Referring to the examples set forth in the previous drawings, stage 580 may be carried out by an inspection machine such as inspection machine 210, or by a posterior inspection module (which may be another inspection machine), such as posterior inspection module 280. For example, if the inspected object is indeed a wafer, the inspection image may be obtained using Electron Beam Inspection (EBI) in a first resolution, while the potential defects selected, based on the way in which they were classified, may be further inspected in much higher resolution by a Defect Review Scanning Electron Microscope (DRSEM).

The wafer (or specific dies thereof) may be declared as operational or nonoperational based on the high resolution inspection of the selected potential defects. Inspecting only potential defects classified based on the mask, while not inspecting other potential defects (which may be located in "uninteresting" areas of the wafers) saves time and resources, and may also improve the results of the inspection. For example, scanning less areas of the wafer would lead to less accumulation of electrical charge resulting from the electrons beamed by the electron beam scanning apparatus.

Referring to method 500 as a whole, it may include correlating areas of a runtime inspection image of a wafer to a template (this stage is also referred to as "template anchoring"). Based on this correlation, areas of the inspection image are selected and later upsampled to provide areas which correspond to the mask. While the determining of the mask may be a relatively long process, as it may serve for runtime inspection of many inspected wafers (or any other inspected objects)—the runtime inspection in such a scenario should be relatively quick (because it is repeated many times). In order to achieve this rapidity, the inspection may be carried out in a relatively low resolution.

It should be noted that while providing additional information useful for the classification process, method 500 does not necessitate any increase in the runtime inspection time, and that while it may provide information in sub-pixel accuracy, it does not require any reduction of the runtime inspection pixel size.

It is noted that while the examples above pertain to electron beam scanning, the disclosed techniques may also be implemented for other types of inspection or imaging (e.g. optical, Radar, sonar, etc.). Likewise, while some of the examples above pertain to inspection of an electronic circuit such as wafers, the disclosed techniques may also be implemented for other types of inspection objects, whether in the nanometric scale or in other scales.

As mentioned above, the template and the mask utilized in method 500 may be created in different ways. For example, the mask may be determined based on a reference image of an inspected-object reference area. The method in such a case, as will be discussed below, may include downsampling at least a portion of the reference image to provide the template which has a lower resolution. It is noted that apart from downsampling, the generating of the template may also include additional types of image processing.

The inspected-object reference area may be a part of the same inspected object (e.g. another die in the same wafer), or may belong to another inspected object (e.g. another wafer of the same batch, or of another batch). The reference image in such a case may be generated by the same inspection machine used for the obtaining of the inspection image of method 500. In another implementation, the reference-image may be generated from computer-aided design (CAD) data.

The creating of the mask and/or the template used in method 500 may be carried out according to the process of method 600.

Figure 8:
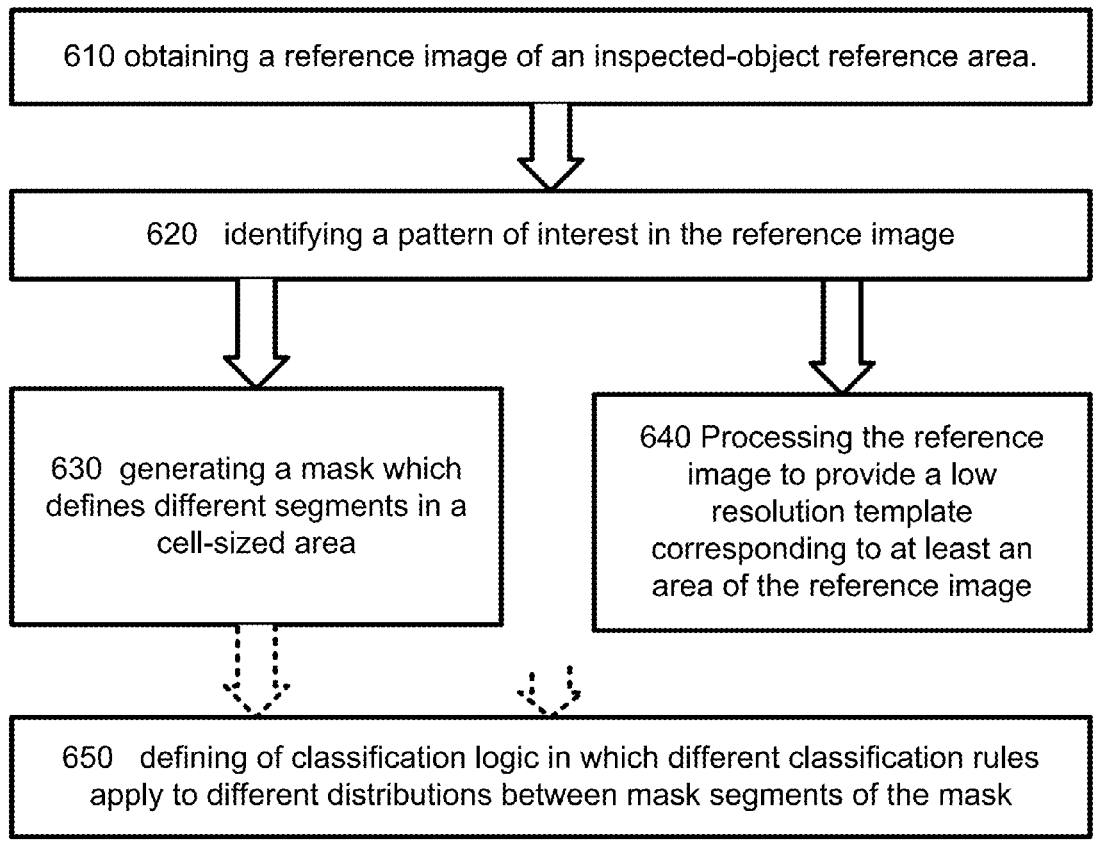
FIG. 8 illustrates a method for generating reference data that may be used for classification, according to an embodiment of the invention.

FIG. 8 illustrates method 600 for generating reference data that may be used for classification (e.g. as in method 500), according to an embodiment of the invention.

Method 600 starts with stage 610 of obtaining a reference image of an inspected-object reference area. If the reference image is an image of an actual object (and is not based on CAD data, for example), a high resolution image of the reference object (which may be selected from a group consisting of an electronic circuit, a wafer, and a photomask, but not necessarily so) may be obtained—either by direct scanning, inspecting, etc., or by receiving the same from another system. The high resolution image may include imaging data of the entire reference object, or just of the reference area. Referring to the examples set forth in the previous drawings, stage 610 may be carried out by an inspection results interface such as inspection results interface 204, or by an inspection machine such as inspection machine 210.

For example, the high resolution reference image may be an image of a die, or of a part of a die. The high resolution reference image may be gathered from a high-resolution inspection process and/or from a computer-aided design (CAD) file. By way of example, if the high-resolution image is gathered by increasing resolution on the e-beam inspection tool or by using a SEM imaging system.

Once the high-resolution image is obtained, it may be used for the definition of information which may later be used in the actual classification of detected possible defects. Method 600 may continue with stage 620 of identifying a pattern of interest in the reference image. Such a pattern of interest is also referred to as a "Golden Cell". Such a pattern of interest may be identified by a person or may be automatically generated. It is noted that such a pattern or "Golden Cell" may be repeated multiple times in the inspection image (possibly in a periodical recurrence pattern), but this is not necessarily so. Referring to the examples set forth in the previous drawings, stage 620 may be carried out by an image processing module such as image processing module 230.

Stage 630 of method 600 includes generating a mask which defines different segments in a cell-sized area. In the case of a reference image that includes a repeating pattern, the size of the cell may be substantially similar to that of the repeating pattern (or to a sub-area thereof, e.g. one which is defined as the pattern of interest in stage 620). It is noted that in some implementations, the size of the mask may be smaller than that of the repeating pattern (possibly significantly so) or larger than the size of the repeating pattern). Referring to the examples set forth in the previous drawings, stage 630 may be carried out by a mask generation module such as mask generation module 290 of system 200.

Within the mask, different segments are defined. Such different segments may be defined for different reasons. For example, segments may be defined to correspond to different functionalities of the electronic circuit (or other item) at the corresponding area or other areas of interest within the Golden Cell pattern. In another example, segments may be defined to correspond to different susceptibility to defects. The number of areas defined in the mask may be different for different inspected objects (e.g. for different electronic circuits), and may be different depending on the usefulness of classification based on such segments to the detection and/or analysis of defects at a later time.

For example, while in some implementations the number of distinct segments in the mask may be three, five, or eight, in other implementations dozens and even hundreds of areas may be defined. The defining of the mask segments may be carried out by a person or by a computer (e.g. based on CAD data).

It should be noted that if indeed the mask is generated in a resolution higher than that which is later used for the runtime inspection in method 500, the segments of the mask are defined in stage 630 at a relatively high resolution (e.g. at the resolution of the high-resolution reference image). While in some implementations the segments defined in the mask are non-overlapping and cover between them the entire area of the mask, this is not necessarily so and some areas of the mask may not belong to any segment.

It should be noted that while the runtime inspection in method 500, in which the identified items (e.g. the potential defects) will be classified, may be carried out in a relatively lower resolution (e.g. having a pixel size corresponding to ×2, ×3 or more the high resolution pixel size), the utilization of a high resolution mask (together with upsampling of part of the inspection image) enables classification of such identified items based on their locations in relation to the higher-resolution mask—which is far more exact.

If indeed the resolution of the reference image is higher than that of the inspection image used in method 500, method 600 may further include stage 640 of processing the high-resolution reference image to provide a lower resolution template corresponding to at least an area of high-resolution image. Apart from downsampling at least a part of the reference image, the generating of the template may include implementation of additional image processing techniques such as softening, smoothing, edge enhancements etc. According to an embodiment of the invention, this step is mandatory if the mask is defined on a resolution that differs from the inspection resolution used for the generating of the inspection image of method 500. Referring to the examples set forth in the previous drawings, stage 640 may be carried out by an image processing module such as image processing module 230 of system 200.

The processing of stage 640 may be implemented by a decimation image processing algorithm or other down-sampling algorithm, but this is not necessarily so. The template (also referred to as "lower resolution reference image") may be used for detection of the recurring pattern (e.g. by identifying a part of it, an anchor) in a run-time inspection image, and therefore for determining a spatial correlation between the mask and the run-time inspection image.

Optionally, the resolution of the template may be lower than that of the mask (and of the high-resolution image), and corresponds to the intended run-time inspection resolution. More than one template may be generated, e.g. in different lower resolutions—to be used in different runtime inspection resolutions. By way of example, the resolution of the template may have a pixel size (height or width) corresponding to 100 nm while the mask resolution may have a pixel size corresponding to 70 nm. An example of a processing of part of the high-resolution reference image to provide a lower resolution template is exemplified in FIG. 9.

The ratio between the 1-D pixel dimension between the template and the mask may differ in various implementations of the invention (e.g. 1:2, 1:4, 1:7, 1:15, etc.). It is noted that the ratio between the corresponding pixel areas is a second power of that ratio (e.g. 1:4, 1:16, 1:49, etc.).

Method 600 may further include stage 650 of defining of classification logic in which different classification rules apply to different distributions between mask segments of the mask. The defining of the classification rules may depend on the specific mask defined, but not necessarily so. For example, the classification rules may be defined based on the relative portion covered by each of the segment types in the mask. Alternatively, the classification rules may be irrespective of the specific mask, and be defined (as part of method 600 or otherwise) based on other considerations—such as the physical characteristics represented by each of the types of segments.

Any stage of method 600 may be carried out by a person (especially using a computer), by a computer or other machine, and/or by a combination thereof.

Figure 9:
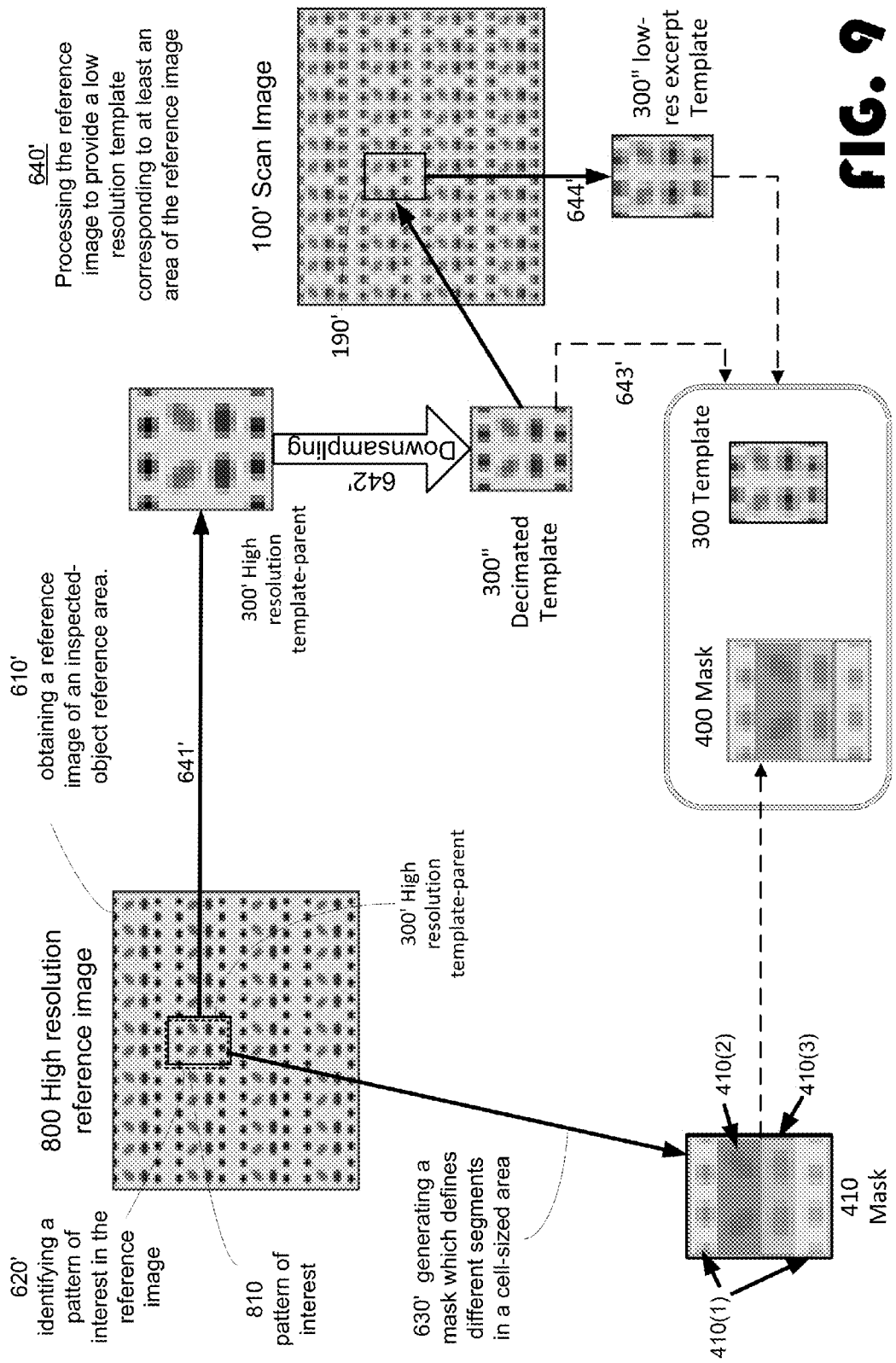
FIG. 9 illustrates a process for generating reference data that may be used for classification, according to an embodiment of the invention.

FIG. 9 illustrates a process 600' for generating reference data that may be used for classification (e.g. as in method 500), according to an embodiment of the invention. Especially, process 600' may be used for the generation of a mask 400 and a template 300.

The stages denoted with an apostrophe (e.g. 610', 620', etc.) are possible implementations of the corresponding stages of method 600 (e.g. stages 610 and 620 respectively).

Referring to stage 640' of processing the reference image to provide a low resolution template corresponding to at least an area of the reference image, it is noted that it may be implemented in several ways, some of which are illustrated.

Firstly, a high resolution template-parent 300' is selected from the reference image 800. The selection is denoted 641'. The high resolution template-parent 300' may be identical to selected cell-sized pattern of interest area 810, or different therefrom. The high resolution template-parent 300' is then decimated or otherwise downsampled or manipulated—e.g. by applying morphological image processing techniques such as smoothing or edge enhancement (denoted 642'), to provide lower-resolution template 300" (also denoted "downsampled template" and "decimated template"). This template 300" may optionally be used "as is" as the template provided (this option denoted 643').

In another implementation (denoted 644'), the downsampled template 300" is used for selecting from a lower resolution image 100' (e.g. in the resolution in which the inspection image of method 500 is obtained) an area 190' that matches the downsampled template 300", and using that area 190' as the template 300.

Reverting to system 200 and to method 500 as a whole, it is noted that utilization of system 200 and/or of method 500 may be implemented to enable ultra-fine pattern-based classification, which in turn facilitates better control of the defect detection process and of the analysis thereof.

In accordance with an aspect of the presently disclosed subject matter, there is yet further provided a program storage device readable by machine, tangibly embodying a program of instructions executable by the machine to perform a method for classifying a potential defect identified within an inspection image of an inspected object, the method comprising the steps of determining an anchor location with respect to the inspection image, based on a matching of a template and a portion of the inspection image, wherein an accuracy of the determining of the anchor location exceeds a resolution of the inspection image; based on a mask which defines different segments within an area and on the anchor location, determining a distribution of the potential defect with respect to one or more of the segments; and classifying the potential defect based on the distribution.

In accordance with an embodiment of the presently disclosed subject matter, there is yet further provided a program storage device, wherein the inspected object is selected from a group consisting of an electronic circuit, a wafer, and a photomask.

In accordance with an embodiment of the presently disclosed subject matter, there is yet further provided a method, wherein the determining of the distribution comprises determining the distribution at an accuracy which exceeds the resolution of the inspection image.

In accordance with an embodiment of the presently disclosed subject matter, there is yet further provided a program storage device, wherein the different segments correspond to parts of the inspected object having different physical characteristics.

In accordance with an embodiment of the presently disclosed subject matter, there is yet further provided a program storage device, wherein the classifying comprises classifying the potential defect according to a classification in which classes correspond to defect types whose implications on an operability of the inspected object differ.

In accordance with an embodiment of the presently disclosed subject matter, there is yet further provided a program storage device, comprising determining multiple anchor locations with respect to the inspection image, based on matching of the template and multiple portions of the inspection image; wherein accuracies of the determining of the multiple anchor locations exceed the resolution of the inspection image; based on the mask and on the multiple anchor locations, determining distributions of the potential defect with respect to one or more of the segments; and classifying the potential defect based on multiple distributions determined for it.

In accordance with an embodiment of the presently disclosed subject matter, there is yet further provided a program storage device, further comprising selecting for further scanning potential defects which are classified into certain classes, wherein the selecting includes refraining from selecting potential defects classified into at least one class other than the certain classes; and selectively scanning, in a resolution which is higher than the resolution of the inspection image, at least one area of the inspected object which is selected based on locations of the potential defects which are selected.

In accordance with an embodiment of the presently disclosed subject matter, there is yet further provided a program storage device, wherein the mask is determined based on a reference image of an inspected-object reference area, wherein the method further comprises generating the template, wherein the generating comprises downsampling a part of the reference image.

In accordance with an embodiment of the presently disclosed subject matter, there is yet further provided a program storage device, wherein the reference image is generated from computer-aided design (CAD) data.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

It will be appreciated that the embodiments described above are cited by way of example, and various features thereof and combinations of these features can be varied and modified.

While various embodiments have been shown and described, it will be understood that there is no intent to limit the invention by such disclosure, but rather, it is intended to cover all modifications and alternate constructions falling within the scope of the invention, as defined in the appended claims.

What is claimed is:

1. An analysis system for classifying possible defects identified within an inspection image of an inspected object, the system comprising:
    a storage device; and
    a processor, coupled to the storage device, to:
    match a template and a portion of the inspection image, thus giving rise to a matching portion of the inspection image, wherein the inspection image is captured by an inspection tool;
    determine, using a mask corresponding to the template and defining one or more segments within the matching portion of the inspection image, a location of a potential defect with respect to the one or more segments, thus giving rise to a matching segment of the inspection image, the matching segment corresponding to the location of the potential defect; and
    classify the potential defect based on the matching segment, thereby considering the location of the potential defect with regard to the respective segment defined within the inspection image,
    wherein the processor is further to define the mask based on a reference image of an inspected-object reference area, to downsample a part of the reference image, and to generate the template based on a result of the downsampling, the reference image and the mask are characterized by a resolution exceeding a resolution of the inspection image.

2. The system according to claim 1, wherein the inspected object is selected from a group consisting of an electronic circuit, a wafer, and a photomask.

3. The system according to claim 1, wherein the processor is further to determine the location of the potential defect with respect to the one or more segments at an accuracy which exceeds the resolution of the inspection image.

4. The system according to claim 1, wherein at least two segments among the one or more segments correspond to parts of the inspected object having different physical characteristics.

5. The system according to claim 1, wherein the processor is to classify the potential defect according to a classification in which at least two classes corresponding to different segments among the one or more segments characterize defect types whose implications on an operability of the inspected object differ.

6. The system according to claim 1, wherein the processor is further to select for further scanning potential defects which are classified into certain classes, wherein the selecting includes refraining from selecting potential defects classified into at least one class other than the certain classes; wherein the system further comprises an inspection module, configured to selectively scan, in a resolution which is higher than the resolution of the inspection image, at least one area of the inspected object which is selected based on locations of selected potential defects.

7. A computerized method for classifying a potential defect identified within an inspection image of an inspected object, the method comprising:
- matching a template and a portion of the inspection image, thereby determining a matching portion of the inspection image, wherein the inspection image is captured by an inspection tool;
- using a mask corresponding to the template and defining one or more segments within the matching portion of the inspection image for determining a location of the potential defect with respect to the one or more segments, thus giving rise to a matching segment of the inspection image, the matching segment corresponding to the location of the potential defect; and
- classifying the potential defect based on the matching segment, thereby considering the location of the potential defect with regard to the respective segment defined within the inspection image,
- wherein the mask is determined based on a reference image of an inspected-object reference area, the method further comprises generating the template, wherein the generating comprises downsampling a part of the reference image, and wherein the reference image and the mask are characterized by a resolution exceeding a resolution of the inspection image.

8. The method according to claim 7, wherein the inspected object is selected from a group consisting of an electronic circuit, a wafer, and a photomask.

9. The method according to claim 7, wherein the determining of the location of the potential defect with respect to the one or more segments is provided at an accuracy which exceeds the resolution of the inspection image.

10. The method according to claim 7, wherein the classifying comprises classifying the potential defect according to a classification in which at least two classes corresponding to different segments among the one or more segments characterize defect types whose implications on an operability of the inspected object differ.

11. The method according to claim 7, wherein the reference image and/or the mask are generated from computer-aided design (CAD) data.

12. A non-transitory computer readable storage medium having instructions that, when executed by a processor, cause the processor to perform a method for classifying a potential defect identified within an inspection image of an inspected object, the method comprising:
- matching a template and a portion of the inspection image, thereby determining a matching portion of the inspection image, wherein the inspection image is captured by an inspection tool;
- using a mask corresponding to the template and defining one or more segments within the matching portion of the inspection image for determining a location of the potential defect with respect to the one or more of the segments, thus giving rise to a matching segment of the inspection image, the matching segment corresponding to the location of the potential defect; and
- classifying the potential defect based on the matching segment, thereby considering the location of the potential defect with regard to the respective segment defined within the inspection image,
- wherein the mask is determined based on a reference image of an inspected-object reference area, and the template is generated using downsampling a part of the reference image, wherein the reference image and the mask are characterized by a resolution exceeding a resolution of the inspected image.

13. The non-transitory computer readable storage medium according to claim 12, wherein the determining the location of the potential defect with respect to the one or more segments comprises determining the location at an accuracy which exceeds the resolution of the inspection image.

14. The non-transitory computer readable storage medium according to claim 12, wherein the classifying comprises classifying the potential defect according to a classification in which at least two classes corresponding to different segments among the one or more segments characterize defect types whose implications on an operability of the inspected object differ.

* * * * *